United States Patent [19]

Kikumoto et al.

[11] 4,071,559

[45] Jan. 31, 1978

[54] PHARMACEUTICALLY ACTIVE 2-OMEGA-AMINOALKOXYDIPHENYLS

[75] Inventors: Ryoji Kikumoto, Machida; Akihiro Tobe, Kawasaki; Shinji Tonomura, Tokyo; Hidenobu Ikoma, Kawasaki; Kazuo Honda, Yokohama, all of Japan

[73] Assignee: Mitsubishi Chemical Industries Limited, Tokyo, Japan

[21] Appl. No.: 676,871

[22] Filed: Apr. 14, 1976

[30] Foreign Application Priority Data

June 19, 1975 Japan ................................ 50-74741

[51] Int. Cl.$^2$ ............................................. C07C 93/06
[52] U.S. Cl. ......................... 260/570.7; 260/326.5 M; 260/501.18; 260/501.19; 424/248.58; 424/274; 424/316; 424/330; 544/106
[58] Field of Search ...................... 260/501.18, 501.19, 260/570.7

[56] References Cited

U.S. PATENT DOCUMENTS

| 2,187,723 | 1/1940 | Alquist et al. ..................... 260/570.7 |
| 2,217,660 | 10/1940 | Alquist et al. ..................... 260/570.7 |
| 3,213,140 | 10/1965 | Mills ................................... 260/570.7 |
| 3,532,712 | 10/1970 | Biel et al. ....................... 260/570.7 X |
| 3,634,507 | 1/1972 | Boissier et al. ............... 260/570.7 X |

*Primary Examiner*—Robert V. Hines
*Attorney, Agent, or Firm*—Oblon, Fisher, Spivak, McClelland & Maier

[57] ABSTRACT

2-Omega-aminoalkoxydiphenyls are prepared and found useful as pharmaceutical agents, particularly as antidepressants.

5 Claims, No Drawings

PHARMACEUTICALLY ACTIVE 2-OMEGA-AMINOALKOXYDIPHENYLS

BACKGROUND OF THE INVENTION

Field of the Invention

This invention relates to 2-omega-aminoalkoxydiphenyl and derivatives thereof which are pharmacologically active as antidepressants.

SUMMARY OF THE INVENTION

This invention relates to compounds of the formula (I):

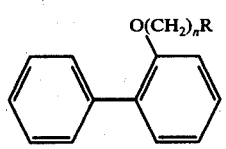

(I)

wherein R is selected from the group consisting of amino, $C_1$–$C_5$ alkylamino, $C_2$–$C_6$ dialkylamino, morpholino, and 1-pyrrolidinyl; n is an integer of 4 or 5; and the pharmaceutically acceptable acid addition salts of said compound.

This invention also relates to a method for palliating conditions of depression in warm-blooded animals which comprises administering to said animal an antidepressant effective amount of a compound of Formula I.

DESCRIPTION OF THE INVENTION

As summarized above, this invention relates to a group of compounds useful as pharmaceutical agents, which compounds are represented by Formula I above. Illustrative of the compounds of this invention are the following:

2-(4-aminobutoxy)diphenyl
2-(4-methylaminobutoxy)diphenyl
2-(4-ethylaminobutoxy)diphenyl
2-(4-isopropylaminobutoxy)diphenyl
2-(4-dimethylaminobutoxy)diphenyl
2-(5-aminopentyloxy)diphenyl
2-(5-dimethylaminopentyloxy)diphenyl
2-(4-morpholinobutoxy)diphenyl
2-(4-(1-pyrrolidinyl)butoxy)diphenyl The pharmaceutically acceptable acid addition salts of the above compounds are, of course, also included within the scope of this invention.

It will be understood that the term "pharmaceutically acceptable acid addition salts" as used herein is intended to include non-toxic salts of the compounds of this invention with an anion. Representative of such salts are hydrochlorides, hydrobromides, sulfates, phosphates, nitrates, acetates, succinates, adipates, propionates, tartrates, maleates, citrates, benzoates, toluenesulfonates, and methanesulfonates.

Of the compounds of this invention, it will be understood that the following compounds are most preferred due to their high level of antidepressant activity and their low level of toxicity.
2-(4-methylaminobutoxy)diphenyl
2-(4-aminobutoxy)diphenyl
2-(4-dimethylaminobutoxy)diphenyl

PREPARATION

The compounds of this invention are prepared by reacting an omega-halogenoalkoxydiphenyl with an amine. The omega-halogenoalkoxydiphenyl starting materials can be prepared by reacting 2-hydroxydiphenyl with 1,4-dihalogenobutane or 1,5-dihalogenopentane in the presence of an alkali.

The amine starting materials include ammonia; primary amines such as methylamine, ethylamine, isopropylamine and the like; secondary amines such as dimethylamine, diethylamine, N-methylethylamine and the like; morpholine; and pyrrolidine. The amine reacts with the equimolecular amount of the omega-halogenoalkoxydiphenyl. However, the use of the excess amine accelerates the reaction. Normally, the amount of the amine to be employed is in the range of 1 to 100 moles per mole of the omega-halogenoalkoxydiphenyl.

The reaction can be carried out without an added solvent. However, the use of a reaction-inert solvent makes the homogenous reaction possible.

Examples of such solvents are water, dioxane, tetrahydrofuran, dimethyl sulfoxide, lower aliphatic alcohols and the mixture thereof.

The reaction temperature is not critical, but normally ranges from room temperatures to 150° C.

The reaction time varies widely with the reaction temperature and the reactivity of the starting materials, but normally is in the range of from 10 minutes to 40 hours. The presence of bases which neutralize a hydrogen halide formed in the course of the reaction accelerates the reaction.

Examples of such bases are inorganic bases such as potassium hydroxide, sodium hydroxide, potassium carbonate, sodium carbonate and the like; and tertiary amines such as pyridine, triethylamine and the like.

The amount of the base to be employed is normally in the range of 1 to 5 moles per mole of the omega-halogenoalkoxydiphenyl.

When the base is absent, the omega-aminoalkoxydiphenyls react with a hydrogen halide formed during the reaction, and are converted to the acid addition salts thereof.

Acid addition salts of the 2-omega-aminoalkoxydiphenyls may be conveniently prepared by contacting the compounds with a suitable acid.

The 2-omega-aminoalkoxydiphenyls and the acid addition salts thereof may be purified by recrystallization employing a suitable solvent such as alcohol-ether.

Pharmacological testing of the 2-omega-aminoalkoxydiphenyls has demonstrated that they are useful as antidepressant agents as evidenced by their ability to reverse reserpine hypothermia in mice.

Anticonvulsant activity has also been found in the compounds of this invention.

The compounds have been tested in mice for antidepressant, sedative, anticonvulsant and anticholinergic activity. The compounds were administered intraperitoneally and the activities of the compounds were compared with those of Amitriptyline.

Antidepressant activity was evaluated by antagonism of reserpine (5 mg/kg i.p.) induced hypothermia (P.S.J. Spencer in "Antidepressant Drugs" S. Garattini and M.N.G. Duhes, ed., Excerpta Medica Foundation, Amsterdam, pages 194–204 (1967)) and antireserpine activity was expressed as relative potency (Amitriptyline = 1).

LD50 was calculated by Litchfield-Wilcoxon method. CNS depressant activity was defined by the ability of the compounds to cause neurological deficit as measured by traction test (S. Courvoisier, R. Ducrot, L. Julou; "Psychotropic Drugs" ed. by S. Garattini, V.

Ghetti, page 373, (1957)) and spontaneous motor activity (Spontaneous motor activity was measured by ANIMEX apparatus). Anticonvulsant activity was determined by antagonism of electroshock induced tonic extensor (L. S. Goodman, M. Singh Grewal, W. C. Brown and E. A. Swinyard, J. Pharmacol, Exptal. Therap., 108, 168 (1953)).

Central anticholinergic effect was assessed by testing the tremorine induced tremor in mice (G. M. Everett, L. E. Bloucus and J. M. Sheppard, Science 124 79 (1956)).

Results are summarized in Table I and Table II, in which ED50 is defined as the dose of the test compounds, which prevent 50% of each response.

Table I

Antireserpine Activity in Mice

| Compound | Relative Potency | LD50 (mg/kg i.p.) |
|---|---|---|
| 2-(4-methylaminobutoxy)diphenyl hydrochloride | 0.99 | 78 |
| 2-(4-aminobutoxy)diphenyl hydrochloride | 0.59 | 137 |
| 2-(4-dimethylaminobutoxy)-diphenyl hydrochloride | 0.45 | 100 |
| Amitriptyline | 1.00 | 65 |

Table II

CNS Depressant, Anticonvulsant and Central Anticholinergic Activity in Mice

| Compound | Anti convulsant Activity ED50 (mg/kg i.p.) | Muscle Relaxant Action ED50 (mg/kg i.p.) | Spontaneous Motor Activity Depression ED50 (mg/kg i.p.) | Antitremorine Effect ED50 (mg/kg i.p.) |
|---|---|---|---|---|
| 2-(4-methyl-aminobutoxy)diphenyl hydrochloride | 14 | 40 | 30 | 20 |
| 2-(4-aminobutoxy)diphenyl hydrochloride | 14 | 50 | 40 | 60 |
| Amitriptyine | 16 | 15 | 18 | 4 |

It will be apparent from Tables I and II that 2-(4-methylaminobutoxy)diphenyl exhibits antireserpine activity comparable to that of Amitriptyline, while it exhibits low toxicity, weak CNS depressant and anticholinergic action. The compounds of this invention can be administered by any means that effects palliating conditions of depression in warm-blooded animals.

For example, administration can be parenterally, subcutaneously, intravenously, intramuscularly, or intraperitoneally. Alternatively or concurrently, administration can be by the oral route. The dosage administered will be dependent upon the age, health and weight of the recipient, the extent of depression, kind of concurrent treatment if any, frequency of treatment, and the nature of the effect desired. Generally, a daily dosage of active ingredient compound will be from about 0.5 to 50 mg per kg of body weight. Normally, from 1 to 30 mg per kg per day, in one or more applications per day is effective to obtain the desired result.

The compound of Formula I can be employed in dosage forms such as tablets, capsules, powder packets, or liquid solutions, suspensions, or elixirs, for oral administration, or sterile liquid formulations such as solutions or suspensions for parenteral use. In such compositions, the active ingredient will ordinarily always be present in an amount of at least 0.5% by weight based on the total weight of the composition and not more than 90% by weight. Besides the active ingredient of this invention, the composition will contain a solid or liquid non-toxic pharmaceutical carrier for the active ingredient. In one embodiment of a composition, the solid carrier can be a capsule of the ordinary gelatin type. In the capsule will be from about 30-60% by weight of a compound of Formula I and 70-40% of a carrier. In another embodiment, the active ingredient can be tableted with or without adjuvants, or put into powder packets. These capsules, tablets and powders will generally constitute from about 5% to about 95% and preferably from 25% to 90% by weight of active ingredient. These dosage forms preferably contain from about 5 to about 500 mg of active ingredient, with from about 25 to about 250 mg being most preferred.

The pharmaceutical carrier can be a sterile liquid such as water and oils, including those of petroleum, animal, vegetable or synthetic origin, such as peanut oil, soybean oil, mineral oil, sesame oil, and the like.

In general, water saline, aqueous dextrose and related sugar solutions, and glycols such as ethylene glycol, propylene glycol and polyethylene glycol are preferred liquid carriers, particularly for injectible solutions such as saline will ordinarily contain from about 0.5% to 20% and preferably about 1 to 10% by weight of the active ingredient. As mentioned above, oral administration can be in a suitable suspension or syrup, in which the active ingredient normally will constitute from about 0.5 to 10% by weight. The pharmaceutical carrier in such composition can be a watery vehicle such as an aromatic water, a syrup or a pharmaceutical mucilage.

The following examples are presented to further illustrate the preparation of the compounds of this invention.

EXAMPLE 1

A mixture of 5.0 g of 2-(4-bromobutoxy)diphenyl, 20 ml of 40% dimethylamine aqueous solution, and 100 ml of ethanol is allowed to stand at room temperature for 8 hours. The solvent and excess dimethylamine are distilled in-vacuo, 2N-NaOH aqueous solution is added, and the reaction product is extracted with ether. The ether solution is distilled, 2N-HCl solution is added and the solution is evaporated to dryness.

The residue is recrystallized from ethanol-ether to give 4.1 g (83% yield) of 2-(4-dimethylaminobutoxy)-diphenyl hydrochloride, m.p. 115°–118° C.

Analysis - Calcd. for $C_{18}H_{23}NO \cdot HCl$ (percent): C, 70.68; H, 7.91; N, 4.58 Found (percent): C, 70.95; H, 7.94; N, 4.48

EXAMPLE 2

A solution of 5.0 g of 2-(4-bromobutoxy)diphenyl in 10 g of isopropylamine is allowed to stand at room temperature for 5 hours.

Isopropylamine is evaporated in vacuo, 2N-NaOH aqueous solution is added, and the reaction product is extracted with ether. The ether solution is distilled, 2N-HCl solution is added, and the solution is evaporated to dryness. The residue is recrystallized from ethanol-ether to give 4.5 g (88% yield) of 2-(4-isopropylaminobutoxy)diphenyl hydrochloride, m.p. 172°–177° C.

Analysis - Calcd. for $C_{19}H_{25}ON \cdot HCl$ (percent): C, 71.34; H, 8.19; N, 4.38. Found (percent): C, 70.95; H, 7.94; N, 4.48.

EXAMPLES 3-9

The compounds in the following table were prepared according to the procedure described in Example 1 or 2, using the appropriate starting materials.

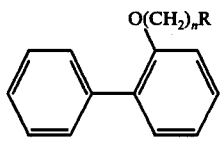

| Example No. | Compound Formula | Addition Moiety | Preparation Process (Ex. No.) | m.p. (° C) | Analysis Upper: Calcd. Lower: Found | | |
|---|---|---|---|---|---|---|---|
| | | | | | C | H | N |
| 3 | O—(CH₂)₄NH₂ (biphenyl) | HCl | 1 | 155–158 | 69.18 / 69.06 | 7.26 / 7.32 | 5.04 / 5.15 |
| 4 | O—(CH₂)₄N(H)(CH₃) (biphenyl) | HCl | 1 | 142–144 | 69.97 / 70.10 | 7.60 / 7.85 | 4.80 / 4.61 |
| 5 | O—(CH₂)₄NHCH₂CH₃ (biphenyl) | HCl | 1 | 146–148 | 70.68 / 71.00 | 7.91 / 8.04 | 4.58 / 4.54 |
| 6 | O—(CH₂)₅N(CH₃)(CH₃) (biphenyl) | HCl | 2 | 98–104 | 71.34 / 71.05 | 8.19 / 7.93 | 4.38 / 4.20 |
| 7 | O—(CH₂)₅NH₂ (biphenyl) | HCl | 1 | 124–126 | 69.97 / 69.85 | 7.60 / 7.72 | 4.80 / 4.69 |
| 8 | O—(CH₂)₄—N(morpholino) (biphenyl) | HCl | 2 | 146–150 | 69.05 / 68.93 | 7.53 / 7.50 | 4.03 / 4.01 |
| 9 | O—(CH₂)₄—N(piperidino) (biphenyl) | HCl | 2 | 153–158 | 72.38 / 72.56 | 7.90 / 8.08 | 4.22 / 4.18 |

Having now fully described the invention, it will be apparent to one of ordinary skill in the art that many changes and modifications can be made thereto without departing from the spirit or scope of this invention as set forth herein.

What is claimed as new and intended to be covered by Letters Patent is:

1. A compound having the formula (I):

wherein R is selected from the group consisting of amino, $C_1$ - $C_5$ alkylamino and $C_2$ - $C_6$ dialkylamino; n is 4; or a pharmaceutically acceptable acid addition salt thereof.

2. The compound of claim 1, wherein R is selected from the group consisting of amino, methylamino, ethylamino and dimethylamino.

3. The compound of claim 1, which is 2-(4-methylaminobutoxy)-diphenyl.

4. The compound of claim 1, which is 2-(4-aminobutoxy)diphenyl.

5. The compound of claim 1, which is 2-(4-dimethylaminobutoxy)-diphenyl.

* * * * *